United States Patent
Ramirez-Vick et al.

(10) Patent No.: US 6,852,493 B2
(45) Date of Patent: Feb. 8, 2005

(54) MAGNETIC FIELD ENHANCED HYBRIDIZATION OF TARGET MOLECULES TO IMMOBILIZED PROBES

(75) Inventors: Jaime E. Ramirez-Vick, Berkeley, CA (US); Simon Chin, Saratoga, CA (US)

(73) Assignee: Iris Biotechnologies, Inc., Santa Clara, CA (US)

( * ) Notice: Subject to any disclaimer, the term of this patent is extended or adjusted under 35 U.S.C. 154(b) by 0 days.

(21) Appl. No.: 09/997,475

(22) Filed: Nov. 19, 2001

(65) Prior Publication Data

US 2002/0164607 A1 Nov. 7, 2002

Related U.S. Application Data

(63) Continuation-in-part of application No. 10/029,113, filed on Dec. 19, 2001, and a continuation of application No. 09/584,661, filed on May 30, 2000, now abandoned, and a continuation-in-part of application No. 09/571,084, filed on May 15, 2000, now abandoned.
(60) Provisional application No. 60/134,110, filed on May 14, 1999.

(51) Int. Cl.$^7$ ............................ C12Q 1/68; C12M 1/00; C07H 21/04
(52) U.S. Cl. ................... 435/6; 435/283.1; 435/287.2; 435/287.9; 435/288.5; 536/23.1
(58) Field of Search .................... 435/6, 283.1, 287.2, 435/287.9, 288.5; 536/23.1; 310/257, 196, 216, 268, 256, 259, 156.05, 258, 217, 218

(56) References Cited

U.S. PATENT DOCUMENTS

| | | | |
|---|---|---|---|
| 5,665,582 A | | 9/1997 | Kausch et al. .............. 435/181 |
| 5,807,522 A | * | 9/1998 | Brown et al. ................. 422/50 |
| 5,807,758 A | | 9/1998 | Lee et al. ................... 436/526 |
| 5,981,297 A | | 11/1999 | Baselt ........................ 436/514 |
| 6,001,573 A | | 12/1999 | Roelant ......................... 435/6 |
| 6,264,825 B1 | * | 7/2001 | Blackburn et al. ....... 205/777.5 |

FOREIGN PATENT DOCUMENTS

| | | |
|---|---|---|
| EP | 0 265 244 | 4/1988 |
| EP | 0 314 500 | 5/1989 |
| WO | WO 91/08480 | 6/1991 |
| WO | WO 95/12808 | 5/1995 |

OTHER PUBLICATIONS

International Research Report for PCT/US00/14969.

* cited by examiner

*Primary Examiner*—BJ Forman
(74) *Attorney, Agent, or Firm*—James A. Fox; Heller Ehrman White & McAuliffe LLP

(57) ABSTRACT

The invention provides a method for increasing the hybridization rate of nucleic acids in a nucleic acid assay by labeling nucleic acid molecules with paramagnetic labels and activating a magnetic field inducing rapid migration of the labeled molecules to a solid support, where the labeled molecule hybridizes with its complementary pair. The paramagnetic label may be present on the target nucleic acid or the probe nucleic acid, depending upon whether the target or probe are the immobile phase.

12 Claims, No Drawings

MAGNETIC FIELD ENHANCED HYBRIDIZATION OF TARGET MOLECULES TO IMMOBILIZED PROBES

This application is a continuation of U.S. patent application Ser. No. 09/584,661, filed May 30, 2000, now abandoned, from which priority is claimed under 35 U.S.C. §120, and is a continuation-in-part of U.S. patent application Ser. No. 09/571,084 filed May 15, 2000, now abandoned, which claims the benefit of U.S. Provisional Application Ser. No. 60/134,110, filed May 14, 1999; and the present application is a continuation-in-part of U.S. patent application Ser. No. 10/029,113, filed Dec. 19, 2001 (a continuation of U.S. patent application Ser. No. 09/571,084, filed May 15, 2000, now abandoned), from all of which non-provisional applications priority is claimed under 35 U.S.C. §120; and the benefit of which provisional application is claimed under 35 U.S.C. §119(e).

BACKGROUND OF THE INVENTION a) Field of the Invention

This invention is related to methods for rapid hybridization of complementary nucleic acid molecules and their use in purification, immunoassays, biosensors, and other biochemical applications.

b) Description of Related Art

The process by which one member of a pair of nucleic acids (oligonucleotides, DNA, RNA) binds its complementary member is known as hybridization. Since nucleic acid molecules have a very strong preference for their sequence complements, simple mixing of complementary sequences is enough to induce them to hybridize. Hybridization is temperature dependent, so nucleic acid molecules that hybridize strongly at low temperatures can be temporarily separated (denatured) by heating. Hybridization is the basis for the polymerase chain reaction and in situ hybridization technologies.

Hybridization is a two step process involving (1) diffusion of the target nucleic acid molecule through the hybridization medium until it reaches an immobilized probe and (2) contact with the probe and binding to its complementary sequence. This process is usually slow because the limited amount of target takes very long to diffuse to the probe surface. The diffusion rate is usually increased by increasing the temperature. Although this increases the hybridization rate, there are limits above which the molecules may be irreparably harmed and the process still requires inordinate amounts of time to complete. Numerous parties have addressed the problem of decreasing cycle time in thermal cyclers and related devices.

The actual hybridization reaction represents the most important and central step in the whole process. The hybridization step involves placing the prepared nucleic acid sample in contact with a specific reporter probe, at a set of optimal conditions for hybridization to occur to the target sequence. Hybridization may be performed in any one of a number of formats. For example, multi-sample nucleic acid hybridization analysis has been conducted on a variety of filter and solid support formats (See G. A. Beltz et al., in Methods in Enzymology, Vol. 100, Part B, R. Wu, L. Grossman, K. Moldave, Eds., Academic Press, N.Y., Chapter 19, pp. 266–308, 1985). One format, the so-called "dot blot" hybridization, involves the non-covalent attachment of target nucleic acids to filters, which are subsequently hybridized with a radioisotope labeled probe(s). "Dot blot" hybridization gained wide-spread use, and many versions were developed (see M. L. M. Anderson and B. D. Young, in Nucleic Acid Hybridization—A Practical Approach, B. D. Hames and S. J. Higgins, Eds., IRL Press, Washington, D.C. Chapter 4, pp. 73–111, 1985). It has been developed for multiple analysis of genomic mutations (D. Nanibhushan and D. Rabin, in EPA 0228075, Jul. 8, 1987) and for the detection of overlapping clones and the construction of genomic maps (G. A. Evans, in U.S. Pat. No. 5,219,726, Jun. 15, 1993).

New techniques are being developed for carrying out multiple sample nucleic acid hybridization analysis on micro-formatted multiplex or matrix devices (e.g., DNA chips) (see M. Baringa, 253 Science, pp. 1489, 1991; W. Bains, 10 Bio/Technology, pp. 757–758, 1992). These methods usually attach specific DNA sequences to very small specific areas of a solid support, such as micro-wells of a DNA chip. These hybridization formats are micro-scale versions of the conventional "dot blot" and "sandwich" hybridization systems. The micro-formatted hybridization can be used to carry out "sequencing by hybridization" (SBH) (see M. Baringa, 253 Science, pp. 1489, 1991; W. Bains, 10 Bio/Technology, pp. 757–758, 1992).

U.S. Pat. No. 5,849,486 teaches the use of electric fields to accelerate hybridization by bringing the negatively charged target molecules close to the immobilized probes. This greatly accelerates hybridization but requires a restricted flow area due to the tendency of the negatively charged DNA to follow the electric field lines, which do not necessarily cross the complementary target DNA location. In order to overcome this problem, the probe DNA has been immobilized within the pores of a polymer such as agarose. Even though this brings the target DNA and the probe DNA in close contact, the movement across the restricted pores slows down the probe because of the high hydrodynamic resistance.

This approach is also nonspecific in nature since the movement of the probe DNA in the electric field depends on the molecule's charge, which varies from molecule to molecule depending upon its sequence. Another problem with this approach is that the metal used in the manufacturing of the electrodes, which generate the electric field, may become magnetized.

The object of the present invention is to provide an improved method for the rapid hybridization of nucleic acids on solid surfaces. Several longstanding problems in purification, immunoassays, biosensors, and other biochemical applications are resolved by this invention.

SUMMARY OF INVENTION

The present invention relates to a method to actively carry out controlled multi-step processing and multiplex reactions. These reactions include, but are not limited to, most molecular biological procedures, such as nucleic acid hybridization, antibody/antigen reaction, and related clinical diagnostics. In addition, the claimed methods are useful for multi-step combinatorial biopolymer synthesis, including, but not limited to, the synthesis of different oligonucleotides or peptides at specific micro-locations on a given device.

The invention provides a method for increasing the hybridization rate of nucleic acids in a nucleic acid assay by labeling nucleic acid molecules with paramagnetic labels and activating a magnetic field inducing rapid migration of the labeled molecules to a solid support, where the labeled molecule hybridizes with its complementary pair. The paramagnetic label may be present on the target nucleic acid or the probe nucleic acid, depending upon whether the target or probe are the immobile phase.

DETAILED DESCRIPTION OF THE INVENTION

I. Definitions

Unless indicated otherwise, the terms defined below have the following meanings:

"Biopolymer" refers to biological molecules such as proteins, oligonucleotides, DNA, etc., which are the basis of hybridization, purification, immunoassays, and many other biochemical applications.

"Hybridization" refers to binding reaction between complementary partners of biopolymer molecules.

"Ligand" refers to one member of the ligand/receptor binding pair, such as, oligonucleotides, DNA, and proteins.

"Nucleic acid molecule" refers to any molecule having at least one nucleic acid moiety, including genomic DNA, cDNA, RNA, PNAs, oligonucleotides, and fragments thereof. The nucleic acid moiety is typically A, C, G, T or U, but may also be another natural or synthetic nucleotide.

"Protein" refers to enzymes, antibodies, and other polypeptides.

The invention provides a method for increasing the hybridization rate of nucleic acids in a nucleic acid assay by labeling nucleic acid molecules with paramagnetic labels and activating a magnetic field which induces rapid migration of the labeled molecules to a solid support, where the labeled molecule hybridizes with its complementary pair. The paramagnetic label may be present on the target nucleic acid or the probe nucleic acid, depending upon whether the target or probe are the immobile phase.

The solid support is selected from the group consisting of silicon, glass, and metals, preferably soft metals selected from the group consisting of silver, copper, gold, platinum (II), mercury, mercury (II), thallium, cadmium (II), platinum (IV) and palladium (II).

The paramagnetic labels may be superparamagnetic particles, having a diameter of from about 1 to about 10 nanometers, or are paramagnetic porphyrins. The paramagnetic labels are attached to the nucleic acid molecules using cleavable conjugating molecules. At least one member of a complementary pair may be labeled with a fluorescent detection molecule.

Paramagnetic agents respond very strongly to magnetic fields, becoming demagnetized after the field is removed. The use of a magnetic field decreases the hybridization time from days to minutes. This prevents the aggregation that would be seen if these paramagnetic agents retained any degree of magnetization.

This invention describes a device fabricated using photolithographic techniques that produces localized DC magnetic fields. These fields are localized at multiple locations on a substrate and are surrounded by coils. These locations are microwells connected by channels to distribute the target DNA hybridization solutions.

The use of paramagnetic agents to concentrate biomolecules using DC magnetic fields is known in the art. The paramagnetic agents currently used are either polymeric capsules with a paramagnetic iron oxide core, beads in which the paramagnetic material is distributed throughout the polymer material, or particles made-up of the paramagnetic material. These agents range in size from a few micrometers to nanometers. The main problem with the use of these agents for hybridization of DNA is their size, since the paramagnetic agent is thousands of time larger than the DNA molecule. This limits the labeled probe DNA accessibility to the immobilized target DNA on the surface and also saturates the available surface for hybridization.

An option to the use of these paramagnetic agents is the use of porphyrin molecules. Molecules of various porphyrins consist of a fundamental skeleton of four rings linked together to form a larger ring. The rings are basically of the pyrole type, four carbon atoms and one nitrogen atom; depending on the porphyrin, various other atoms are connected to the large ring. Moreover, atoms of various metals positioned in the center of the large ring distinguish different porphyrins. Molecules with Gd(III) as the metal ion are currently used as contrast agents for magnetic resonance imaging. Their widespread use as contrast agents is because of their paramagnetic properties. Their paramagnetic properties and size (equivalent to a fluorescent molecule) makes Gd(III) porphyrins ideal candidates for paramagnetic labels of DNA molecules.

The following claims are presented to specifically point out and distinctly claim the invention. All documents mentioned in this disclosure are incorporated herein by reference.

What is claimed is:

1. A method for increasing the hybridization rate of nucleic acids in a nucleic acid assay, said method comprising:
   a) providing probe nucleic acid molecules of known sequence attached to a solid support within multiple microwells, said microwells being at multiple locations on said support and being surrounded by coils suitable for producing localized DC magnetic fields within said microwells, said microwells being connected by channels, said solid support being selected from the group consisting of silicon, glass, and metals that is or is coated with a metal selected from the group consisting of silver, copper, gold, platinum (II), mercury, mercury (II), thallium, cadmium (II), platinum (IV) and palladium (II);
   b) providing target molecules consisting essentially of nucleic acid molecules labeled with paramagnetic labels having a diameter of from about 1 nanometer (nm) to about 10 nm;
   c) attracting said labeled nucleic acid target molecules to the solid support by activating said coils to provide a localized DC magnetic field within each of said microwells effective to induce rapid migration of said labeled nucleic acid target molecules;
   d) hybridizing the labeled nucleic acid target molecules with their complementary pairs at a hybridization rate greater than the hybridization rate in the absence of said attracting by said localized DC magnetic fields within each of said microwells;
   e) washing the support and inverting the polarity of the localized DC magnetic fields within each of said microwells to remove any unbound or nonspecifically bound molecules; and
   f) detecting the hybridized target nucleic acid molecules.

2. A method of claim 1 in which the paramagnetic labels comprise superparamagnetic particles.

3. A method of claim 1 in which the paramagnetic labels comprise paramagnetic porphyrins.

4. A method of claim 1 in which the paramagnetic labels are attached to the nucleic acid molecules using cleavable conjugating molecules.

5. A method of claim 1 in which the nucleic acid molecules are oligonucleotides, genomic DNA, cDNA, RNA or fragments thereof.

6. A method of claim 1 in which at least one of said probe nucleic acid molecule and said nucleic acid target molecule is labeled with a fluorescent detection molecule.

7. A method for increasing the hybridization rate of nucleic acids in a nucleic acid assay, said method comprising:

a) providing nucleic acid target molecules attached to a solid support within multiple microwells, said microwells being at multiple locations on said support and being surrounded by coils suitable for producing localized DC magnetic fields within said microwells, said microwells being connected by channels, said solid support being selected from the group consisting of silicon, glass, and metals that is or is coated with a metal selected from the group consisting of silver, copper, gold, platinum (II), mercury, mercury (II), thallium, cadmium (II), platinum (IV) and palladium (II);

b) providing probe molecules consisting essentially of nucleic acid molecules of known sequence labeled with paramagnetic labels having a diameter of from about 1 nanometer (nm) to about 10 nm;

c) attracting said labeled nucleic acid probe molecules to the solid support by activating said coils to provide a localized DC magnetic field within each of said microwells effective to induce rapid migration of said labeled nucleic acid probe molecules;

d) hybridizing the labeled nucleic acid probe molecules with their complementary pairs at a hybridization rate greater than the hybridization rate in the absence of said attracting by said localized DC magnetic fields within each of said microwells;

e) washing the support and inverting the polarity of the localized DC magnetic fields within each of said microwells to remove any unbound or nonspecifically bound molecules; and f) detecting the hybridized probe nucleic acid molecules.

8. A method of claim 7 in which the paramagnetic labels comprise superparamagnetic particles.

9. A method of claim 7 in which the paramagnetic labels comprise paramagnetic porphyrins.

10. A method of claim 7 in which the paramagnetic labels are attached to the nucleic acid molecules using cleavable conjugating molecules.

11. A method of claim 7 in which the nucleic acid molecules are oligonucleotides, genomic DNA, cDNA, RNA or fragments thereof.

12. A method of claim 7 in which at least one of said probe nucleic acid molecule and said nucleic acid target molecule is labeled with a fluorescent detection molecule.

\* \* \* \* \*